United States Patent [19]
Quay et al.

[11] Patent Number: 5,897,851
[45] Date of Patent: *Apr. 27, 1999

[54] NUCLEATION AND ACTIVATION OF A LIQUID-IN-LIQUID EMULSION FOR USE IN ULTRASOUND IMAGING

[75] Inventors: Steven C. Quay; Dean R. Kessler, both of Edmonds; Ronald A. Roy, Kirkland; Dilip Worah, Bothell, all of Wash.

[73] Assignee: Sonus Pharmaceuticals, Inc., Bothell, Wash.

[*] Notice: This patent issued on a continued prosecution application filed under 37 CFR 1.53(d), and is subject to the twenty year patent term provisions of 35 U.S.C. 154(a)(2).

[21] Appl. No.: 08/659,201

[22] Filed: Jun. 5, 1996

Related U.S. Application Data

[63] Continuation-in-part of application No. 08/477,462, Jun. 7, 1995.

[51] Int. Cl.$^6$ .................................................. A61K 49/04
[52] U.S. Cl. ............................................ 424/9.52; 424/9.5
[58] Field of Search ................................ 424/9.52, 9.51, 424/9.5, 450, 455; 128/662.02; 600/458

[56] References Cited

U.S. PATENT DOCUMENTS

| | | |
|---|---|---|
| 3,900,420 | 8/1975 | Sebba . |
| 4,265,251 | 5/1981 | Tickner . |
| 4,276,885 | 7/1981 | Tickner et al. . |
| 4,442,843 | 4/1984 | Rasor et al. . |
| 4,466,442 | 8/1984 | Hilmann et al. . |
| 4,533,254 | 8/1985 | Cook et al. . |
| 4,572,203 | 2/1986 | Feinstein . |
| 4,657,756 | 4/1987 | Rasor et al. . |
| 4,681,119 | 7/1987 | Rasor et al. . |
| 4,684,479 | 8/1987 | D'Arrigo . |
| 4,718,433 | 1/1988 | Feinstein . |
| 4,774,958 | 10/1988 | Feinstein . |
| 4,832,941 | 5/1989 | Berwing et al. . |
| 4,844,882 | 7/1989 | Widder et al. . |
| 4,865,836 | 9/1989 | Long, Jr. . |
| 4,957,656 | 9/1990 | Cerny et al. . |
| 5,141,738 | 8/1992 | Rasor et al. . |
| 5,147,631 | 9/1992 | Glajch et al. . |
| 5,228,446 | 7/1993 | Unger et al. . |
| 5,305,757 | 4/1994 | Unger et al. . |
| 5,310,540 | 5/1994 | Giddey et al. . |
| 5,334,381 | 8/1994 | Unger . |
| 5,348,016 | 9/1994 | Unger et al. . |
| 5,352,436 | 10/1994 | Wheatley et al. . |
| 5,393,524 | 2/1995 | Quay . |
| 5,409,688 | 4/1995 | Quay . |
| 5,413,774 | 5/1995 | Schneider et al. . |
| 5,425,366 | 6/1995 | Reinhardt et al. . |
| 5,425,580 | 6/1995 | Beller . |
| 5,540,909 | 7/1996 | Schutt ................................ 424/9.52 |
| 5,542,935 | 8/1996 | Unger et al. ............................ 604/190 |
| 5,558,094 | 9/1996 | Quay . |
| 5,558,853 | 9/1996 | Quay . |
| 5,558,854 | 9/1996 | Quay . |
| 5,558,855 | 9/1996 | Quay . |
| 5,573,751 | 11/1996 | Quay . |
| 5,578,292 | 11/1996 | Schneider et al. . |
| 5,580,575 | 12/1996 | Unger et al. . |
| 5,585,112 | 12/1996 | Unger et al. . |
| 5,592,940 | 1/1997 | Kampfe et al. . |
| 5,595,687 | 1/1997 | Raynolds et al. . |
| 5,595,723 | 1/1997 | Quay . |
| 5,597,549 | 1/1997 | Schneider et al. . |
| 5,605,673 | 2/1997 | Schutt et al. . |

FOREIGN PATENT DOCUMENTS

| | | |
|---|---|---|
| 0 359 246 | 3/1990 | European Pat. Off. ........ A61K 49/00 |
| 0 467 031 A2 | 1/1992 | European Pat. Off. ........ A61K 49/00 |
| 0 554 213 | 1/1992 | European Pat. Off. ........ A61K 49/00 |
| 4-43889 | 7/1992 | Japan ............................ A61K 49/00 |
| WO 92/17212 | 10/1992 | WIPO ........................... A61K 49/00 |
| WO 92/17213 | 10/1992 | WIPO ........................... A61K 49/00 |
| WO 93/00930 | 1/1993 | WIPO ........................... A61K 49/04 |
| WO 93/05819 | 4/1993 | WIPO ........................... A61K 49/00 |
| WO 94/16739 | 8/1994 | WIPO ........................... A61K 49/00 |
| WO 94/21301 | 9/1994 | WIPO ........................... A61K 49/00 |
| WO 94/21302 | 9/1994 | WIPO ........................... A61K 49/00 |
| WO 94/28780 | 12/1994 | WIPO ............................ A61B 8/00 |
| WO 94/28797 | 12/1994 | WIPO ............................ A61B 8/00 |
| WO 94/28873 | 12/1994 | WIPO ........................... A61K 9/127 |
| WO 94/28939 | 12/1994 | WIPO ........................... A61K 49/00 |
| WO 95/01187 | 1/1995 | WIPO ........................... A61K 49/00 |
| WO 95/03835 | 2/1995 | WIPO ........................... A61K 49/00 |

OTHER PUBLICATIONS

Cotter, et al., "Myocardial Opacificaition by Low Doses EchoGen in Patients: Assessment of Preactivation by Closed Syringe Suction", JACC Feb. 1996, vol. 27, p. 126A (abstract).

V.E. Zelenetskii et al., "Manufacture of Syringes from Polymeric Materials", Med. Tekh., vol. 6, No. 2, 1972, pp. 30–33 (abstract No. 118172).

Ophir, Jonathan, et al., Contrast Agents in Diagnostic Ultrasound. Ultrasound in Medicine and Biology 15:319–333, 1989.

Zarif, L., et al., Synergistic Stabilization of Perfluorocarbon–Pluronic F–68 Emulsion by Perfluoroalkylated Polyhydroxylated Surfactants. JAOCS 66:10, Oct. 1989.

Swanson, D., et al., Chapter 22: Enhancement Agents for Ultrasound: Fundamentals. Pharmaceuticals in Medical Imaging: Radiopaque Contrast Media Radiopharmaceuticals Enhancement Agents for Magnetic Resonance Imaging and Ultrasound (1990).

Serratrice, G. et al., Co–Solubilisation De Fluorocarbures et D'eau En Présence de Nouveaux Tensioactifs Non Ioniques Fluorés. Journal Chim. Phys. 87:1969–1980, 1990.

*Primary Examiner*—José G. Dees
*Assistant Examiner*—Michael G. Hartley
*Attorney, Agent, or Firm*—Limbach & Limbach L.L.P.

[57] ABSTRACT

A method of activating an ultrasound contrast agent such that an increased number of microbubbles are produced and subsequent ultrasound images using the activated agent is enhanced. Hypobaric methods are disclosed which provide significant increases in bubble population per unit volume over unactivated solutions. The method is particularly useful for the activation of the dispersed phase in a gas or liquid in liquid emulsion.

8 Claims, 2 Drawing Sheets

NUCLEATION AND ACTIVATION OF A LIQUID-IN-LIQUID EMULSION FOR USE IN ULTRASOUND IMAGING

RELATED APPLICATION

This application is a continuation-in-part application of pending U.S. patent application Ser. No. 08/477,462 filed Jun. 7, 1995, the contents of which are incorporated herein by reference.

FIELD OF THE INVENTION

This invention relates to methods for nucleating gas-in-liquid or liquid-in-liquid colloidal dispersions or emulsions of microbubble precursors for more effective use in ultrasound imaging. It also relates to activation of preexisting microbubbles in solutions for more effective use in ultrasound imaging. More specifically, the invention concerns methods by which the formation of gaseous microbubbles is promoted in such dispersions prior to or during their introduction into the animal being imaged.

BACKGROUND OF THE INVENTION

Various contrast agents for use in diagnostic ultrasound, including echocardiography, have been described. A review of the subject is found in Ophir and Parker, *Ultrasound in Med. & Biol.* (1989), 15:319–333, although research has intensified since its publication.

In more recent years, agents which include gaseous microbubbles or microbubble precursors (as opposed to completely solid or liquid agents) have become the subject of great interest, since these agents take advantage of the relatively high echogenicity of gases versus liquids or solids.

To enhance the performance of microbubbles as ultrasound contrast agents, numerous approaches have been disclosed. These approaches are generally directed to methods by which either the persistence of the bubbles is increased or the bubble size population is optimized.

For example, such approaches include the use of solid particulates into which the bubbles are infused before use (e.g. U.S. Pat. No. 5,147,631), and the use of encapsulants or stabilizers for the microbubbles (such as human serum albumin, e.g. U.S. Pat. No. 4,718,433), each of which is incorporated by reference herein.

Another approach has been to identify compounds which, as gases, are relatively more persistent in blood than air (e.g. U.S. Pat. Nos. 5,393,524 and 5,409,688 and U.S. patent application Ser. No. 08/380,085, having the same assignee as the present application), and the use of a select number of such gases which are normally liquids at manufacturing temperatures but gases in the body in liquid-in-liquid dispersions (e.g. U.S. patent applications Ser. No. 08/008,172, Ser. No. 08/148,284 and Ser. No. 08/182,024, also assigned to the assignee of the present application) all of which are hereby incorporated by reference.

One method of producing microbubbles in a solution for use with ultrasound imaging is to disperse a gas in a liquid according to U.S. Pat. No. 4,832,941 by manual suspension, e.g., by spraying the liquid backwards and forwards in the gas atmosphere 25 times via a three-way tap.

Also, the use of ultrasound energy to promote the formation of microbubbles for use in ultrasound contrast is known both from U.S. Pat. No. 4,572,203 to Feinstein (prior to administration) and Molecular Biosystem's WO 94/28939 (in vivo, after administration), both of which are incorporated by reference herein. Neither of these methods, however, produce microbubbles capable of visualizing myocardial perfusion with a peripheral injection.

While such approaches have improved the quality and usefulness of diagnostic ultrasound contrast, further enhancements which provide even better images are desirable.

SUMMARY OF THE INVENTION

To meet this need, this invention is directed to a hypobaric method of activating a gas-in-liquid dispersion, a liquid-in-liquid dispersion, or a mixed gas-liquid-in-liquid dispersion (such dispersions may also contain additional carriers or stabilizers), so that greater numbers of bubbles are formed in a desired size range. Further, the invention relates to methods of ultrasound imaging which include the activating process of the invention prior to administration of the agent. The methods of the invention surprisingly provide improved bubble populations and stability over prior methods.

DETAILED DESCRIPTION OF THE INVENTION

Figure 1:
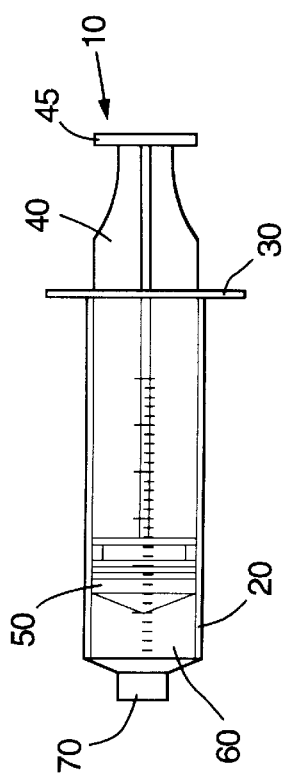
FIG. 1 shows a syringe for use in an activation unit according to the present invention.

The invention will best be understood by the description of specific embodiments, keeping in mind that the claimed invention is not to be construed as limited to the examples described here. As will be understood from these examples, the activation process of the invention provides enhancement of the contrast in an ultrasound image generated during medical or veterinary diagnosis.

Definitions

To ensure a complete understanding of the invention the following definitions are provided:

Surfactants: The group of amphiphilic materials which are manufactured by chemical processes or purified from natural sources or processes. These can be anionic, cationic, nonionic, and zwitterionic. Such materials are described in Emulsions: Theory and Practice, Paul Becher, Robert E. Krieger Publishing, Malabar, Fla., 1965 which is hereby incorporated by reference.

Amphiphilic Material: A substance which is strongly adsorbed at an interface and which normally produces a dramatic reduction in the interfacial tension with small changes in the bulk phase concentration. Examples include synthetic surfactants, naturally occurring materials such as biocompatible proteins, lipids, sterols, alginates, cellulose derivatives, and finely divided organic or inorganic particulate solids.

Polyoxypropylene-Polyoxyethylene Glycol Nonionic Block Copolymers: The surfactants which are available from BASF Performance Chemicals, Parsippany, N.J. under the trade name Pluronic and which consists of the group of surfactants designated by the CTFA name of poloxamer 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403.

Fluorine-Containing Surfactant: A surfactant containing one or more fluorine atoms. Some, but not necessarily all, fluorine containing surfactants useful in this invention can be selected from the group consisting of: telomer B containing fluorinated surfactants available from Du Pont, Wilmington, Del. under the Trade name of Zonyl (including Zonyl FSA, FSP, FSE, UR, FSJ, FSN, FSO, FSC, FSK, and TBS), the fluorochemical surfactants from 3M Industrial Chemical Products Division, St. Paul, Minn. under the trade name of Fluorad (including FC-95, FC-98, FC-143, FC-170C, FC-171, FC-430, FC-99, FC-100, FC-120, FC-129, FC-135, FC-431, FC-740), the perfluoroalkylpoly (oxyethylene) surfactants described by Mathis et al. (*J Am Chem Soc* 106, 6162–6171 (1984), incorporated herein by reference), the fluoroalkylthio-etherpoly(oxyethylene) surfactants described by Serratrice et al. (*J Chim Phys* 87, 1969–1980 (1990), incorporated herein by reference), the perfluoroalkylated polyhydroxylated surfactants of Zarif et al. (*J Am Oil Chem Soc* 66, 1515–1523 (1989), incorporated herein by reference), the fluorosurfactants available from Atochem North America, Philadelphia, Pa. under the trade name of Forafac.

Activation: A method step by which bubble formation, specifically microbubble formation, is encouraged or promoted when that step is applied to a solution which is to be administered as an ultrasound contrast agent. More specifically, activation within the meaning of the invention refers to the application of a hypobaric force on a solution which contains microbubbles or microbubble precursors to cause microbubble production, size change or additional microbubbles of gas to form in said solution.

Microbubble Precursor: a microbubble nuclei, i.e., any solid or liquid particle or gaseous macrobubble which is capable of producing microbubbles of a gas contained therein under the conditions referred to herein as activation conditions.

Colloidal Dispersion: A system having at least one substance as a solid, liquid or gas (the dispersed phase) which is immiscible and finely divided and distributed evenly throughout at least one second substance which forms the dispersion medium or continuous liquid phase.

Biocompatible: Capable of performing functions within or upon a living organism in an acceptable manner, without undue toxicity or physiological or pharmacological effects.

High Vapor Pressure Chemical: A chemical with a sufficiently high vapor pressure that colloidal dispersions of the chemical as a liquid contain, at the body temperature of an organism undergoing an ultrasound examination, a sufficient quantity of the chemical as a gaseous dispersion to provide a diagnostically useful alteration in the ultrasound data obtained during an examination. High vapor pressure chemicals include low boiling liquids, a preferred embodiment of the present invention. Chemicals with vapor pressures at ambient temperature of above 20 Torr (typically having boiling points below 135° C.) are another preferred embodiment. The latter class of chemicals which are useful in this invention include, but are not limited to: perfluorinated n-alkanes, cycloalkanes, and branched alkyl compounds containing up to nine carbons (nonane; B. P. 125° C.); alkyl hydrocarbons containing up to ten carbons, such as n-decane; ethers, other organic halides, and alcohols.

Fluorine-Containing Compounds: A compound containing at least one fluorine atom.

Emulsion: A colloidal dispersion of one immiscible liquid dispersed in another liquid in the form of droplets, whose diameter, in general, are between 100 and 3000 nm and which is typically optically opaque, unless the dispersed and continuous phases are refractive index matched. Such systems possess a limited stability, generally defined by the application or relevant reference system, which may be enhanced by the addition of amphiphilic materials or viscosity enhancers.

Microemulsion: A stable liquid monophasic and optically isotropic colloidal dispersion of water and water-immiscible liquids stabilized by amphiphilic materials in which the dispersions have appreciable light scattering properties (meaning they can appear optically clear or milky but are reddish or yellowish if observed by transmitted light) and the diameters of the particles are, in general, between 5 and approximately 140 nm.

Organic Particulate Solids: include sugars, proteins, amino acids, lipids, nucleic acids, and others.

Inorganic Particulate Solids: include aluminas, carbonates, bicarbonates, silicates, aluminasilicates, phosphates, and others.

Aqueous Medium: A water-containing liquid which can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials.

Agents With Which The Method May Be Used

The activation method of the invention can be used on any emulsion, dispersion, or liquid (e.g. gas-in-liquid, liquid-in-liquid and surfactant containing liquids) in which it is desired that bubble formation be promoted or enhanced. Further, there may be instances when the activation method can be used to advantage when the solution on which the activation step is performed would not strictly be considered a dispersion or emulsion, but when bubble activation will nevertheless advantageously occur. For example, agents which incorporate a solid carrier, whether organic or inorganic, can be advantageously subjected to activation according to the invention. Additionally, solutions which contain stabilizers (such as amphiphilic material including human serum albumin or surfactant solutions), which might not strictly be considered dispersions, can likewise be advantageously activated by the invention.

Gases which may be the subject of activation will be selected from those already known in ultrasound contrast, keeping in mind that biocompatible compounds which are more persistent are preferred. Thus, gases of fluorine-containing chemicals can especially be used.

The activation process is particularly advantageous when used with gas or liquid-in-liquid emulsions or dispersions. Expected to be of particular value are those dispersions described in applications Ser. No. 08/008,172, Ser. No. 08/148,284 and Ser. No. 08/182,024, each of which is incorporated herein by reference, in which the dispersed phase is liquid at common processing and storage temperatures, but which forms a gas, at least in part, at the body temperature of the animal in which the agent will be used.

The activation process is also advantageous when used with the dispersions described in applications PCT WO 95/03835, PCT WO 94/28939, WO 94/28797, WO 94/28780, and U.S. Pat. No. 4,832,941, each of which is incorporated herein by reference.

In a further preferred embodiment, the process will be applied to liquid-in-liquid colloidal dispersions in which the continuous phase is aqueous and the dispersed phase is a fluorine containing, branched or linear, hydrocarbon. In this class, the most preferred dispersed phase compounds will be $C_1$–$C_8$ fluorine substituted hydrocarbons, due to their biocompatibility, and the fact that they have boiling points below the body temperatures of animals of interest and/or have vapor pressures high enough (even if they boil above such temperatures) to provide microbubbles in quantities sufficient to enhance ultrasound contrast in use.

Even more particularly preferred are emulsions in which the dispersed phase is selected from one or a mixture of the following: sulfur hexafluoride; tetrafluoromethane; perfluoroethane; perfluoropropane; perfluorobutane; perfluoropentane; perfluorohexane; and perfluoroheptane and perfluorooctane and mixtures or derivatives thereof.

Activation Method

In order to provide enhanced ultrasound contrast, the activation method will provide a means by which bubbles of a desired size population are formed prior to administration of the bubbles in the body. Methods of activation according to the invention include approaches which may be considered under a general category of the application of "hypobaric" forces to the solution in question.

Hypobaric forces are to be distinguished from hydrodynamic or acoustic under standard definitions.

"Hydrodynamic" forces, which can be single pass or multiple pass, are those forces that operate during the generation of bulk motion of fluids. The methods described in U.S. Pat. No. 4,832,941 are an example of such forces.

"Acoustic" forces are those that operate during the propagation of sound waves in a fluid. Generally, continuous or intermittent acoustic energy is applied rather than a single acoustic wave.

"Hypobaric" forces are those that operate during the reduction of hydrostatic pressure in a fluid, result in isotropic stresses, and do not necessarily involve shearing motion, or propagating acoustic fluctuations.

Encompassed by the class of hypobaric forces of the invention are the forces created when the solution is forced rapidly through a filter or when the pressure in the solution is rapidly lowered to below atmospheric by placing the solution in a sealed vessel and rapidly lowering the pressure in the vessel. This is in distinction to the methods in which liquids are stored under higher pressure (above atmospheric) which are released to expose the liquid to atmospheric, not hypobaric, pressures, for example see U.S. Pat. No. 5,334,381.

The invention will be better understood by way of the following examples; however, it is to be understood that these examples are illustrative only and are not to be construed as limiting the invention as claimed below:

EXAMPLE 1

A preferred method of hypobaric activation

A 2.0, 3.0 or 4.0 mL volume of EchoGen® emulsion (Sonus Pharmaceuticals, Bothell, Wash.), a 2% perfluoropentane emulsion described in Ser. No. 08/182,024, was administered intravenously following activation in a patient via an antecubital vein. All solutions of 2% EchoGen® emulsion were injected using sterile syringes using aseptic technique.

Method of Administration

Materials needed:
2% EchoGen® emulsion
Saline for injection
3-way stopcock
10 or 20 mL luer-lock polycarbonate syringe (Merit Medical Systems, South Jordan, Utah)
18 gauge needle
20 gauge angiocath 1. Determine the volume of 2% EchoGen® to be administered.
   If $\leq 2$ mL use a 10 mL syringe with luer-lock for administration
   If >2 mL use a 20 mL syringe with luer-lock for administration
2. Connect a 3 way stopcock and 18 gauge needle to the appropriate size syringe.
3. Withdraw the calculated volume and 1 mL additional of 2% EchoGen® emulsion from the vial.
4. Clear the syringe of air and EchoGen® to achieve the correct administration dosage and turn the stopcock to the closed position to seal the syringe. Remove the needle.
5. Connect a 20 cc saline flush syringe to the 90° port on the 3 way stopcock. Push saline to expel air from the stopcock port.
6. Holding the EchoGen® Emulsion containing syringe by the barrel in a horizontal position, rapidly pull back on the syringe plunger to the extent of the graduations on the syringe (to the 10 mL or 20 mL mark) and immediately release the plunger. This should result in an audible "pop". This audible "pop" is the result of the plunger exciting an acoustic pressure wave in the air behind the advancing plunger. It is not an acoustic mode in the contents of the syringe.
7. Immediately (within 5 seconds) attach the syringe assembly via the stopcock onto the 20 gauge Angiocath located in the patient's antecubital vein.
8. Turn the stopcock to allow EchoGen® emulsion administration and inject.
9. Turn the stopcock to the saline flush syringe and inject 10 mL.

A 0.05 mL/kg dose produced myocardial perfusion in a human subject.

EXAMPLE 2

Comparison of hypobaric and non-hypobaric activation

The objective of this study was to evaluate the hemodynamic parameters and ultrasound imaging effects of EchoGen® 2% Emulsion with a hypobaric pre-activation process following intravenous administration to an anesthetized monkey.

A monkey was anesthetized with ketamine intravenously, intubated, and allowed to spontaneously breathe room air. End tidal $CO_2$ was monitored continuously. A catheter was placed in the femoral artery to monitor blood pressure and to obtain arterial blood samples for blood gas analysis. A 5 French catheter was inserted into the right external jugular vein and advanced into the pulmonary artery for monitoring pulmonary artery pressure. In addition, ECG leads (lead II), a rectal temperature probe and pulse oximeter were attached to the monkey for additional monitoring.

EchoGen® 2% Emulsion was administered via a 20 gauge angiocath inserted into the femoral vein. Peripheral venous injections of EchoGen® were performed following hypobaric activation within the syringe at dosages of 0.05 and 0.1 mL/kg bodyweight. The following parameters were continuously monitored and recorded at designated time points before and after administration: electrocardiograms (lead II), systemic blood pressure (systolic, diastolic, and mean), heart rate, pulmonary artery pressure (systolic, diastolic and mean), end-tidal $CO_2$, $O_2$-saturation, and respiratory rate. Ultrasound imaging was performed before, during and after each injection with an ATL Ultramark 9 with a P7-4 transducer. Images were recorded on SVHS videotape.

The monkey received 9 bolus intravenous administrations of EchoGen® 2% Emulsion at dosages of 0.05 or 0.1 mL/kg at approximately 30 minute intervals. A total of 9 administrations during the study led to a potential maximum cumulative dosage of 7.5 mL or 0.7 mL/kg. At the end of the monitoring period, the animal was euthanized by an intravenous injection of Beuthanasia-D®.

There were no adverse clinical signs or test article-related effects on blood gas parameters, arterial pH, electrocardiograms, respiratory rate, end-tidal $CO_2$, $O_2$-saturation or pulmonary artery pressure.

There were minor, transient test article-related effects on systemic blood pressure. The general effect was a decrease in systolic, diastolic, and mean blood pressures (10–18%) within the first minute following administration of EchoGen® 2% Emulsion which returned to baseline spontaneously within 90 seconds.

Injections at all dosages produced dense right and left cardiac chamber opacification without excessive attenuation of the signal. Following pulmonary transmission, dense myocardial enhancement was observed at dosages of 0.05 and 0.1 mL/kg bodyweight. Ventricular contractions were essentially unchanged and alterations in arterial pressure were transient.

Using non-hypobaric activation through a filter the same level of myocardial enhancement required a dose of 0.6 mL/kg or greater, up to 10-times the above dose.

Under the conditions of the study, dosages of 0.05 and 0.1 mL/kg of EchoGen® 2% Emulsion administered intravenously following hypobaric pre-activation had no significant effect on the cardiovascular parameters measured in an anesthetized monkey expect for a transient, minor decrease in mean systemic arterial blood pressure. The transient decreases in systemic arterial blood pressure (10–18%) returned to baseline within 90 seconds. The hypobaric pre-activation method provided a dramatic improvement in efficacy as evidenced by the dense myocardial enhancement observed at a dosage of 0.05 and 0.1 mL/kg.

In conclusion, the method of hypobaric activation of EchoGen® 2% Emulsion immediately prior to administration is significantly more efficacious for providing dense ultrasound contrast enhancement without significant adverse hemodynamic effects.

EXAMPLE 3

Comparison of the Activation Methods for EchoGen® Emulsion, 2% DDFP: in vitro Bubble Size Analysis The objectives of these experiments were to use bubble size and density measurements using phase Doppler light scattering interferometry to compare activation of EchoGen® Emulsion, in vitro, sonication and hypobaric methods.

We have shown that activation (converting the liquid droplets to microbubbles) prior to administration provides greater efficacy and could permit the use of lower doses. Three methods of activation were compared:

1. Hydrodynamic Filtration: By passing the emulsion droplets through a 1.2 μm filter under pressure, the emulsion will experience a barometric pressure decrease;
2. Sonication; and
3. Hypobaric Sealed Container Method: By placing the emulsion in a sealed syringe and vigorously withdrawing the plunger and then releasing the plunger, one can lower the pressure in the liquid and activate the liquid droplets.

Few methods exist for the determination of the size of gas bubbles. In these experiments the Phase Doppler Interoferrometric (Aerometrics, Inc., Mountain View, Calif.) method of particle sizing was used. This method uses the phase shift of the light transmitted through or reflected from spherical particles and collected at large off axis angles.

The laser phase Doppler particle sizer determines number density using Beer's law for particles of approximately 10 μm in size, the maximum number density is $10^7/cm^3$. When this concentration is exceeded, the instrument cannot obtain reliable data concerning number density or particle size, (this phenomena is similar to attenuation in ultrasound). Bubble concentration from all activation methods exceeded this value when the undiluted drug was activated. Since the activation methods differed in the degree to which the drug was activated by a wide margin, the concentration of each had to be adjusted individually in order to obtain accurate measurement of bubble size and density. Bubble size was determined by activating a small quantity of the drug, 0.1 to 1 mL, diluting it to proper concentration with saline, and delivering it to the cell, (5×1 cm with the sides attached at 72° and 108° angles respectively) where it was isolated by closing the stopcock placed above and pinch clamp placed directly below. The cell was aligned so that the receiving cell was 108° from the sending laser. For particles in the 1–35 μm range, data was obtained every 10 seconds for 1–2 minutes. The data from the first 30 seconds was combined for better statistical relevancy.

Activation Procedures

1. Filtration

Filtration through a 1.2 μm filter. One mL of EchoGen® Emulsion was filtered through a 1.2 μm Acrodisc filter (25 mm flat disc) into 4 mL of saline and the entire mixture (5 mL) was introduced into the cell at the rate of 0.5 mL/s.

2. Sonication

One tenth of 1 mL (0.1 mL) of EchoGen® Emulsion was sonicated at 42 KHz in a 5 mL tubing for 10 seconds with 10 second lag phase following which the material was introduced into the cell with 6 mL saline at the rate of 0.5 mL/s.

3. Hypobaric Activation

One mL was of EchoGen® Emulsion withdrawn into a 10 mL syringe equipped with a 3-way stopcock. The stopcock was set so the syringe barrel was closed. The plunger was rapidly pulled back to the 10 mL mark and allowed to snap back. One tenth of 1 mL (0.1 mL) of the material was introduced into the cell with 6 mL saline at the rate of 0.5 mL/s.

Results

The data for the first 30 seconds for the various methods was averaged and is presented in Table 1.

TABLE 1

Summary of Bubble Measurements

| Activation Method | Volume of EchoGen® | Normalized Mean diameter | Number of Bubbles/mL of EchoGen® Emulsion ×10⁶ |
|---|---|---|---|
| None | 1 | None | <0.1 |
| 1.2 μm Filtration | 1 | 100% | 6.8 |
| Sonication | 0.1 | 98% | 144 |
| Hypobaric Activation | 0.1 | 96% | 78 |

*The actual measured diameters, which are precise but not necessarily accurate, were normalized to the value obtained with the 1.2 μm filter All three methods of activation result in approximately equal microbubble sizes, but the number of particles activated into microbubbles differ considerably. Sonication and hypobaric methods generate approximately 21 and 11 times more bubbles, respectively, than the filtration method and all three methods were superior to unactivated EchoGen® emulsion.

EXAMPLE 4
A preferred hypobaric sealed container construction

In the Hypobaric Sealed Container Method of activation, the solution to be activated is placed in a sealed syringe and the pressure is then reduced by rapidly withdrawing the plunger. The plunger is then immediately released and snaps back to its initial position. This last step generates large pressures in the syringe, 40 to 60 atmospheres, and this may cause problems. In fact, using conventional glass or plastic syringes in this activation method resulted in about a 20% breakage rate of the syringe body. For this reason, it was realized that the sealed container used in the Hypobaric Sealed Container Method of activation must be made of a strain-resistant material. Specifically, the sealed container must be capable of withstanding pressures of at least 40 to 60 atmospheres. Furthermore, the sealed container must be capable of withstanding a pressure change of about 40 to 60 atmospheres occurring over a fraction of a second—the time it takes the plunger to snap back into position. In one embodiment, the sealed container is made of polycarbonate resin. In a preferred embodiment, the sealed container is a polycarbonate syringe, i.e. a syringe with a polycarbonate resin body. For example, Medallion™ brand syringes manufactured by Merit Medical Systems, South Jordan, Utah 84095 may be used. In over 500 trials using these syringes there have been no breakages of the polycarbonate syringe bodies.

EXAMPLE 5
A preferred device for hypobaric activation

Figure 2:
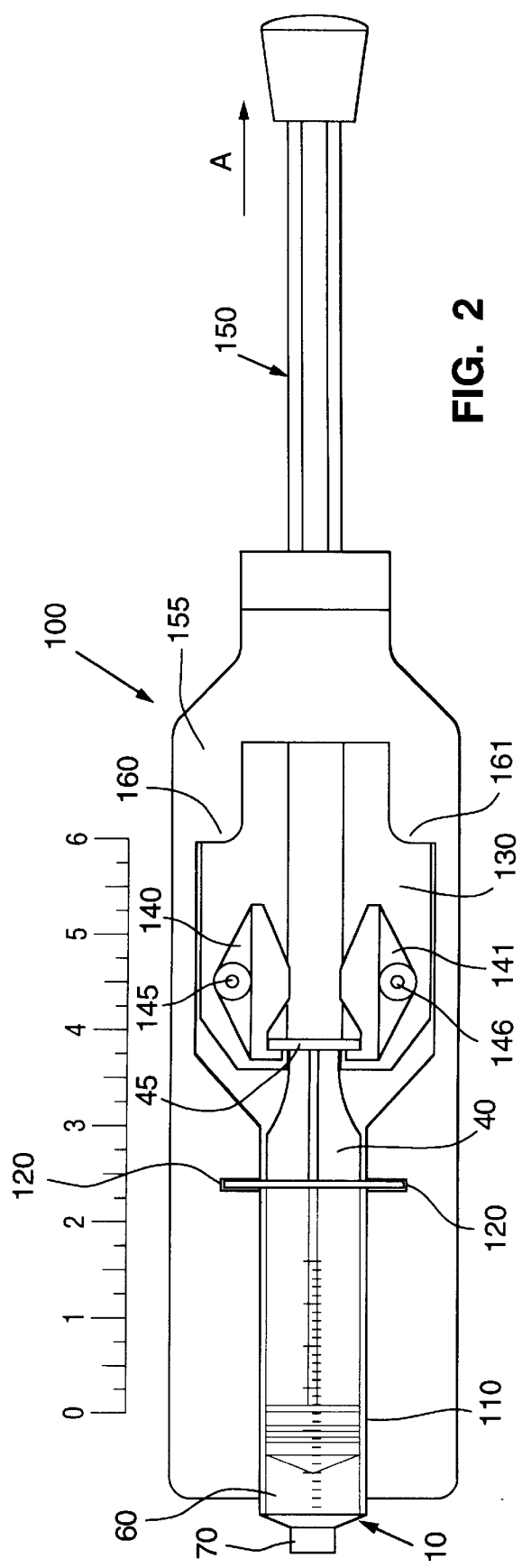
FIG. 2 shows a top view of one embodiment of an activation unit according to the present invention.

FIGS. 1–3 show a preferred device for achieving hypobaric activation according to the present invention.

FIG. 1 shows a standard syringe 10 for use in the present invention. The syringe includes a syringe body 20 having a flange 30, a syringe plunger 40 having a flange 45, and a rubber stopper 50 attached to syringe plunger 40. The solution to be activated is contained in cavity 60. The syringe is filled and discharged through opening 70. As discussed above, it is preferred that the syringe is made of a polycarbonate resin.

FIGS. 2 and 3A–3C show syringe 10 mounted on a hypobaric activation unit 100. The activation unit 100 includes the following elements:

- a syringe stabilizer 110 and slots 120 for holding the syringe body 20 and flanges 30;
- a movable plate 130 attached to a handle 150;
- hooks 140 and 141 mounted on plate 130 and pivoted about pivots 145 and 146, for securing syringe plunger flange 45;
- a frame 155 having shoulders 160 and 161;
- a base 170 to which the syringe stabilizer 110 and frame 155 are fixed and which supports movable plate 130; and
- a spring 180 attached to the base 170 and movable plate 130.

To prepare an activated dose of contrast agent, the operator first places the syringe 10 in the activation unit 100 so that the syringe body 20 is positioned in syringe stabilizer 110 and flanges 30 are positioned in slots 120. The syringe plunger 40 is positioned so that flange 45 is secured by hooks 140 and 141.

After positioning the syringe in the activation unit, the operator fills the syringe with a predetermined amount of the solution to be activated. To achieve the syringe filling step, the operator first connects syringe opening 70 to a supply of the solution to be activated (not shown). The operator then withdraws handle 150 a predetermined amount in direction A shown in FIG. 2. Handle 150 is attached to movable plate 130 which supports hooks 140 and 141. Withdrawing handle 150 in direction A therefore moves hooks 140 and 141 in direction A and this in turn withdraws syringe plunger 40 from syringe body 20 which is restrained from moving by flanges 30 in slots 120. In this way, a predetermined volume of solution is delivered into syringe cavity 60. After filing the syringe, the opening 70 is disconnected from the solution supply and is sealed. Alternatively, the syringe may be filled manually with a predetermined volume of solution prior to being placed in the activation unit. In this case, the above filling step is omitted.

After the syringe has been filled, the solution is activated in the following manner.

Figure 3C:
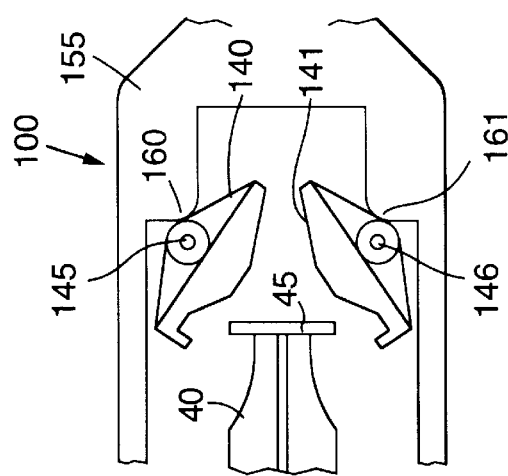
FIG. 3C shows a detailed top view of a part of the activation unit shown in FIG. 3A.
Figure 3A:
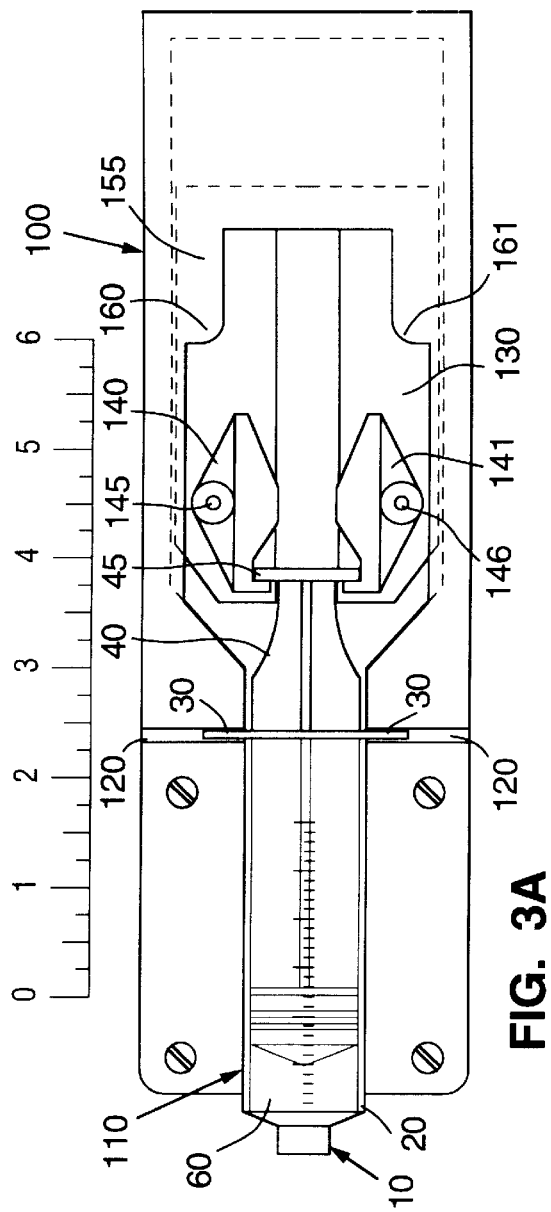
FIG. 3A shows a top view of another embodiment of an activation unit according to the present invention.
Figure 3B:
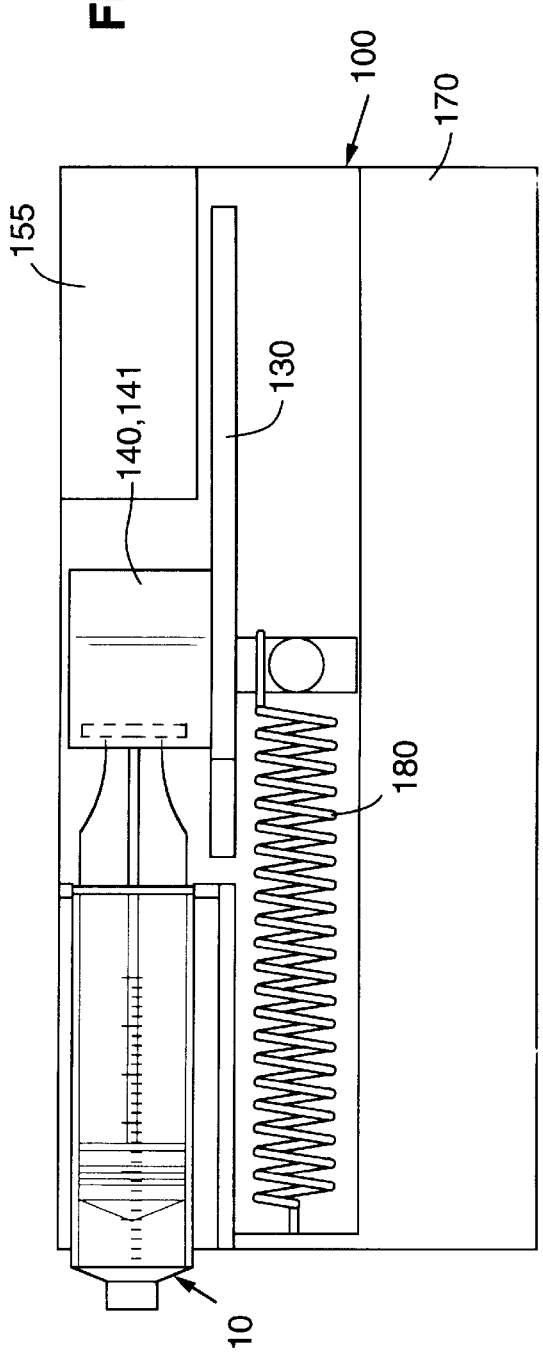
FIG. 3B shows a side view of the activation unit shown in FIG. 3B.

First, the operator rapidly withdraws handle 150 in direction A to its fully extended position. This has the effect of rapidly withdrawing syringe plunger 40 from syringe body 20 which reduces the pressure of the solution contained in cavity 60. When handle 150 is withdrawn to its fully extended position, hooks 140 and 141 contact frame shoulders 160 and 161 and this causes the hooks to pivot into their open position thus releasing syringe plunger 40. FIG. 3C shows the hooks in their open position. When the hooks release the syringe plunger, the reduced pressure in the solution causes the plunger to "pop" back into its unextended position. At this time the solution is activated and is ready to be injected into the subject.

The design of the activation unit shown in FIGS. 2 and 3 ensures that the syringe plunger is always released after it has been withdrawn to a predetermined extension. This feature allows the operator to control the hypobaric conditions used in activating the solution in a precise and consistent manner, thus minimizing operator error and increasing the consistency of the properties of the activated contrast agent.

After the hooks have released the plunger, the operator releases handle 150 and spring 180 then returns plate 130 and hooks 140 and 141 to their starting position ready to receive the next syringe.

What is claimed is:

1. A method of ultrasound imaging comprising the steps of:
   introducing into a syringe a liquid-in-liquid emulsion of dodecafluoropentane dispersed in water;
   sealing the syringe;
   withdrawing a plunger sealing one end of the syringe from a first plunger position to a second plunger position to create a lower than atmospheric pressure over said emulsion and cause the formation of microbubbles of dodecafluoropentane within said emulsion;
   returning the plunger from the second plunger position to the first plunger position by releasing the plunger;
   immediately injecting said microbubble containing emulsion into a subject; and
   performing an ultrasound scan on an anatomical region of the subject into which the emulsion has been delivered.

2. The method according to claim 1 wherein the lower than atmospheric pressure is from 40 to 60 atmospheres.

3. The method according to claim 1 wherein the plunger is returned to the first plunger position from the second plunger position in less than one second.

4. The method according to claim 1 wherein a distance the plunger is withdrawn is sufficient to cause a popping sound when the plunger is released.

5. A method of ultrasound imaging comprising the steps of:

introducing into a syringe a liquid-in-liquid emulsion of dodecafluoropentane dispersed in water;

sealing the syringe;

withdrawing a plunger sealing one end of the syringe from a first plunger position to a second plunger position to create a lower than atmospheric pressure of from 40 to 60 atmospheres over said emulsion;

returning the plunger from the second position to the first position by releasing the plunger;

immediately injecting said microbubble containing emulsion into a subject; and performing an ultrasound scan on an anatomical region of the subject into which the emulsion has been delivered.

6. The method according to claim 5 wherein a distance the plunger is withdrawn is sufficient to cause a popping sound when the plunger is released.

7. A method of ultrasound imaging comprising the steps of:

introducing into a syringe a liquid-in-liquid emulsion of dodecafluoropentane dispersed in water;

sealing the syringe;

reducing the pressure within the syringe to a lower than atmospheric pressure adequate to form microbubbles of dodecafluoropentane dispersed in said emulsion;

releasing the reduced pressure;

immediately delivering said dodecafluoropentane microbubble containing emulsion from said syringe into a subject; and performing an ultrasound scan on an anatomical region of the subject into which the emulsion has been delivered.

8. The method according to claim 7 wherein the lower than atmospheric pressure is from 40 to 60 atmospheres.

* * * * *